(12) United States Patent
Palomo Coll

(10) Patent No.: US 7,060,839 B2
(45) Date of Patent: Jun. 13, 2006

(54) PROCESS FOR THE PREPARATION OF PANTOPRAZOLE AND INTERMEDIATES THEREFOR

(75) Inventor: Alberto Palomo Coll, deceased, late of Barcelona (ES); by Pilar Sturla De Palomo, legal representative, Barcelona (ES); by Deborah Palomo Sturla, legal representative, Barcelona (ES); by Alberto Palomo Sturla, legal representative, Barcelona (ES)

(73) Assignee: Dinamite Dipharma (Dipharma S.P.A.), Basiliano (IT)

(*) Notice: Subject to any disclaimer, the term of this patent is extended or adjusted under 35 U.S.C. 154(b) by 121 days.

(21) Appl. No.: 10/381,978

(22) PCT Filed: Oct. 1, 2001

(86) PCT No.: PCT/EP01/11327

§ 371 (c)(1),
(2), (4) Date: Aug. 19, 2003

(87) PCT Pub. No.: WO02/28852

PCT Pub. Date: Apr. 11, 2002

(65) Prior Publication Data

US 2004/0049044 A1    Mar. 11, 2004

(30) Foreign Application Priority Data

Oct. 2, 2000   (ES) ............................. P200002370

(51) Int. Cl.
*C07D 401/12* (2006.01)

(52) U.S. Cl. .................................................. 548/273.7

(58) Field of Classification Search ............. 546/273.7; 548/273.7
See application file for complete search history.

(56) References Cited

FOREIGN PATENT DOCUMENTS

| AU | 394 368 | 3/1992 |
|---|---|---|
| EP | 0 166 287 | 1/1986 |
| RU | 2 060 541 | 11/1994 |
| WO | WO 01 04109 | 1/2001 |
| WO | WO 01 79194 | 10/2001 |

*Primary Examiner*—Patricia L. Morris
(74) *Attorney, Agent, or Firm*—Young & Thompson

(57) ABSTRACT

A novel process is described for the preparation of the active principle pantoprazole based on the use of novel intermediate compounds of general formula (I)

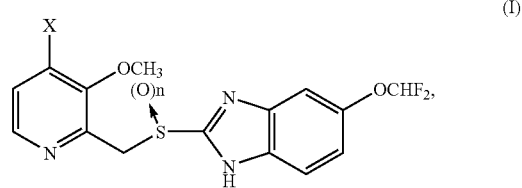

(I)

where X is an atom of halogen and n=0 or 1, so that when n=1, the intermediate compounds are methoxylated, and when n=0 said intermediate compounds are first oxidized to n=1 and thereafter are methoxylated.

Also described are the novel intermediates, as well as the process for the preparation thereof.

4 Claims, No Drawings

PROCESS FOR THE PREPARATION OF PANTOPRAZOLE AND INTERMEDIATES THEREFOR

FIELD OF THE INVENTION

The present invention relates to a process for the preparation of pantoprazole, as well as to the novel intermediate compounds used therein and to the process for the preparation of said intermediate compounds.

PRIOR ART

Pantoprazole is the international non-proprietary name of the chemical product 5-(difluoromethoxy)-2-[[(3,4-dimethoxy-2-pyridinyl)methyl]sulfinyl]-1H-benzimidazole of formula

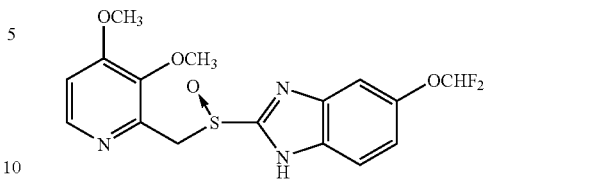

This product is an active ingredient used in the treatment of gastric ulcers, usually in the form of its sodium salt.

The product was described for the first time in European patent application EP-A-0166287 that also describes several processes for the preparation of products assignable to a general formula among which pantoprazole is to be found. The reaction sequences of these processes, applied precisely to the preparation of pantoprazole, are given in Scheme 1.

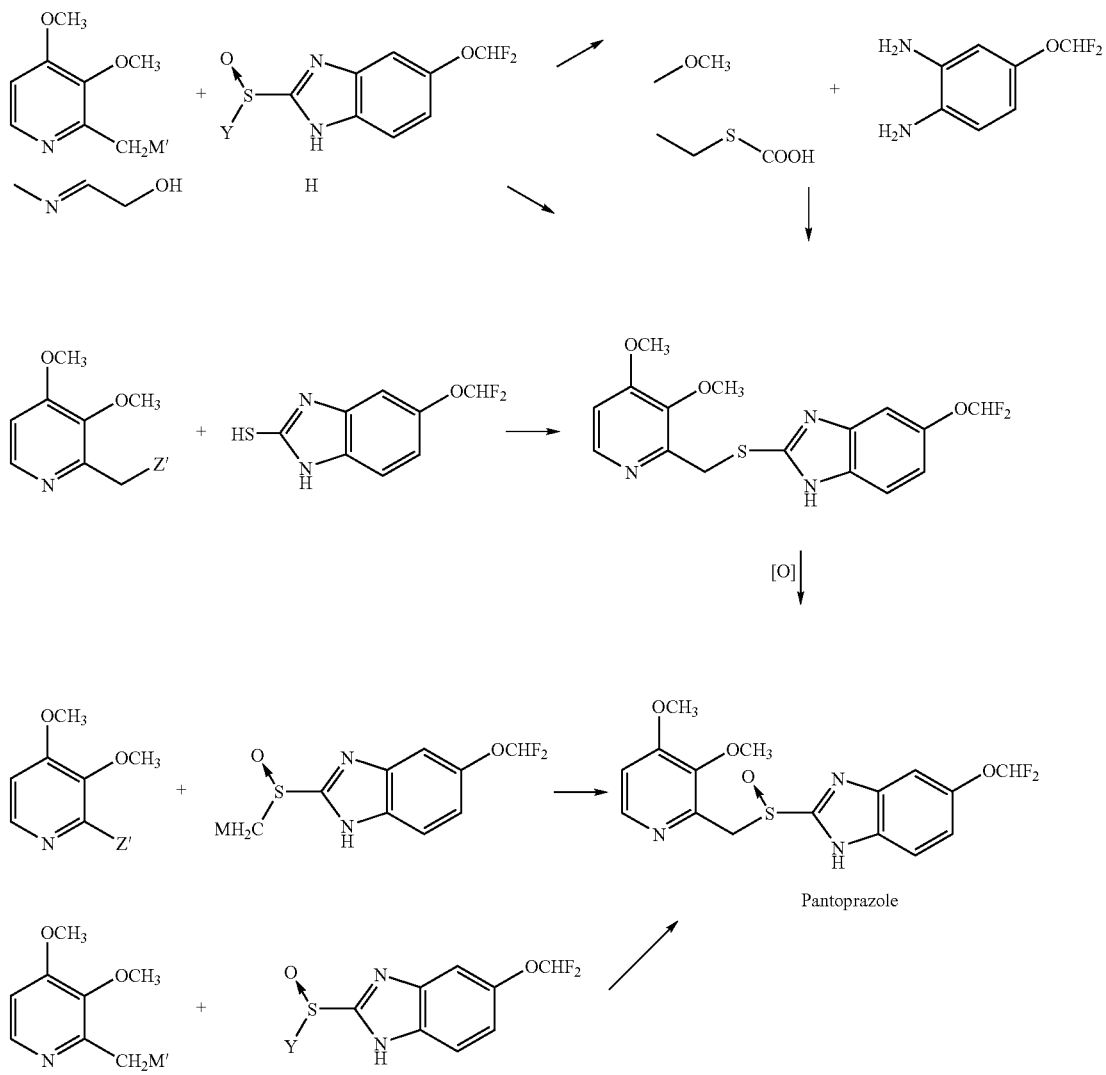

In Scheme 1, the variables Y, Z, Z' and Z" are leaving groups, for example atoms of halogen, and the variables M and M' are atoms of alkali metals.

Austrian patent AT-B-394368 discloses another process based on a different route of synthetis, the reaction sequence of which is given in Scheme 2.

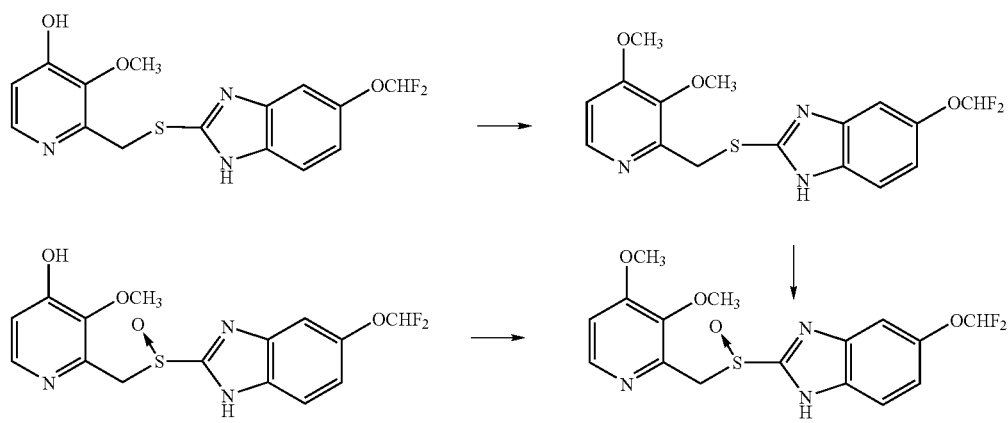

Nevertheless, this process has obvious drawbacks, since the methylation can take place not only in OH in the 4-position of the pyridine ring, but also in the nitrogen linked to a hydrogen of the benzimidazole ring, which can give place to mixtures of the desired product with the two possible methylated isomers of the benzimidazole compounds obtained, 3-methyl or 1-methyl, which means that additional chromatographic purification steps are needed and the yields obtained are low.

PCT application WO97129103 discloses another process for the preparation of pantoprazole, the reaction sequence of which is given in Scheme 3.

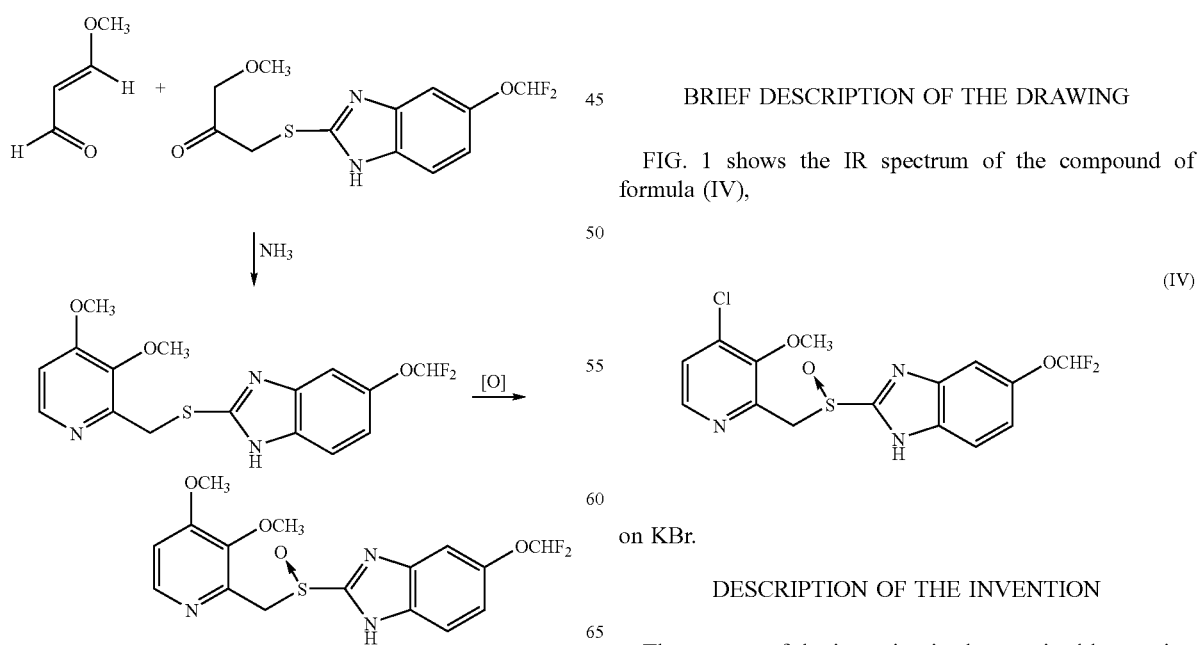

As may be seen, different synthesis strategies have been proposed for the preparation of pantoprazole, some of them recently, which is an indication that the preparation of the product is still not considered to be sufficiently well developed, whereby there is still a need for developing alternative processes that allow pantoprazole to be prepared by means of simpler techniques and more accessible intermediate compounds and with good chemical yields.

SUMMARY OF THE INVENTION

The object of the present invention is a novel process for the preparation of pantoprazole that needs only easily obtainable intermediate compounds.

Also part of the object of the invention are the novel intermediate compounds used in the aforesaid process, as well as the processes for the preparation of such intermediates.

BRIEF DESCRIPTION OF THE DRAWING

FIG. 1 shows the IR spectrum of the compound of formula (IV), (IV)

on KBr.

DESCRIPTION OF THE INVENTION

The process of the invention is characterized by starting from a compound of general formula (I)

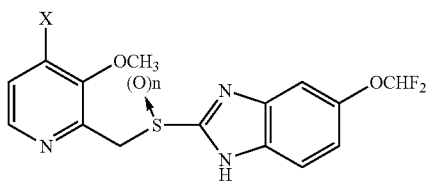

(I)

where X is an atom of halogen and n=0 or 1, and which
a) when n=1, is reacted with a methoxylating agent, or
b) when n=0, is first oxidised to n=1 and thereafter is reacted with the methoxylating agent,
to obtain pantoprazole, of formula (II)

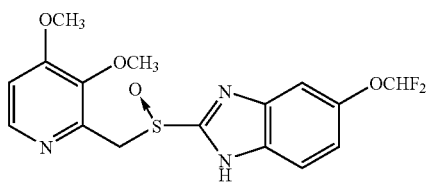

(II)

X is preferably an atom of chlorine.

The methoxylation can be conducted with an alkali metal methoxide, preferably sodium or potassium, or using mixtures of methanol and an alkaline hydroxide, in a polar, preferably aprotic, solvent, such as for example dimethylform, amide, dimethylacetamide and dimethylsulfoxide among others. If desired, the reaction may be completed with the aid of tetrakistriphenylphosphine palladium, holding the reaction temperature within a range comprised between room temperature and 80° C.

It will be evident to one skilled in the art that, if the substituent X corresponds to another leaving group equivalent to an atom of halogen, equivalent results may be obtained.

The oxidation can be conducted in the presence of peracids, as for example the perbenzoic acid, although it is preferable to use ammonium permolybdate or pertungstate, with hydrogen peroxide. An aqueous alcoholic mixture, for example of methanol and water, is appropriate as solvent, and the reaction may be conducted at a temperature ranging from 0° C. to 30° C.

It should be pointed out that the process of the invention overcomes the drawback characteristic of the process of the above mentioned Austrian patent, AT-B-394368, since the methoxylation is selective towards the 4-position of the pyridine ring and does not affect the nitrogen of the benzimidazole ring. This allows better yields and easier-to-purify crude reaction products to be obtained.

The compounds corresponding to the general formula (I)

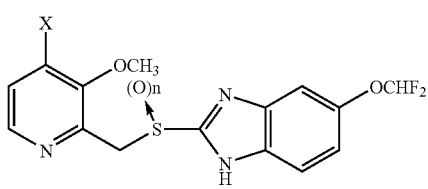

(I)

where X and n have the meaning given above, are novel whereby, as such compounds, they are also part of the object of the invention and, in particular, the compounds corresponding to formulas (III) and (IV) are claimed as novel:

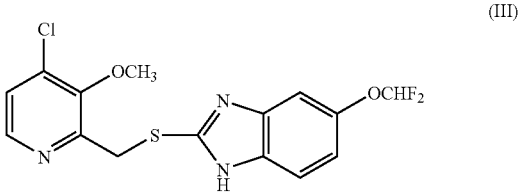

(III)

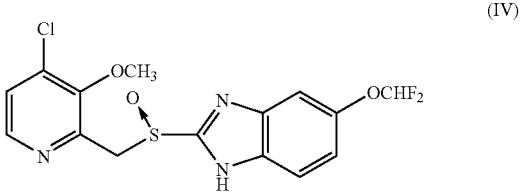

(IV)

Compound (IV) is prepared by oxidation of compound (III), using a method similar to the one already explained, until the corresponding sulfoxide is obtained.

On the other hand, compound (III) can be prepared through the reaction detailed in Scheme 5.

Scheme 5

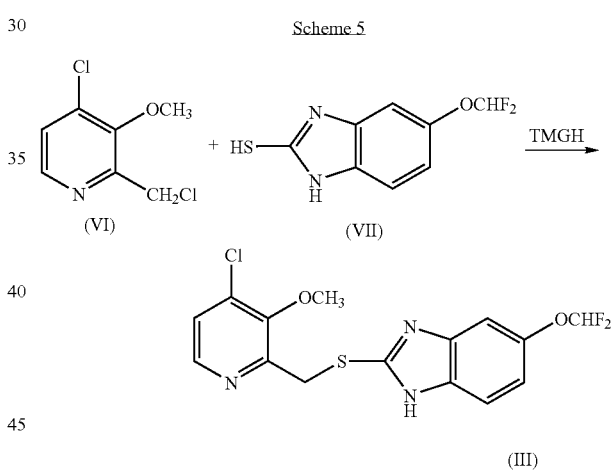

that is to say, reacting the chloromethylpyridine compound (VI) with the mercaptan derivative of benzimidazole (VII), in the presence of a base, such as tetramethylguanidine (TMGH).

In turn, the chloromethylpyridine compound (VI) can be prepared by a process following the reaction sequence of Scheme 6

Scheme 6

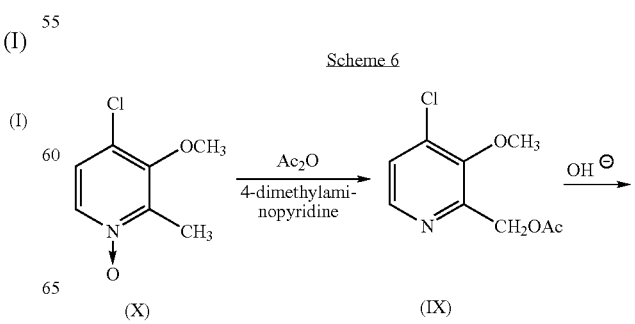

-continued

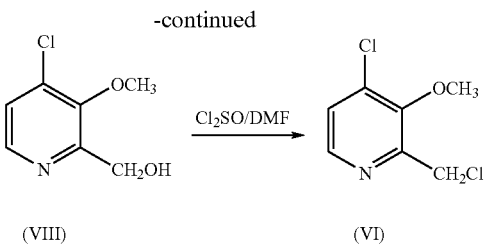

In this way, the starting product 2-methyl-3-methoxy-4-chloropyridine N-oxide (X) is reacted with the acetate salt of formula

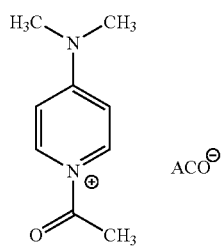

previously formed by reacting acetic anhydride with 4-dimethylaminopyridine, to obtain the acetoxylated compound (IX). Said acetoxylated compound is then hydrolysed in an aqueous alkaline medium to obtain the carbinol (VIII) that is finally reacted with the reactant of formula

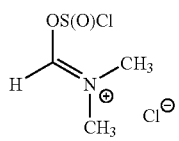

formed by reacting thionyl chloride (SOCl$_2$) with N,N-dimethylformamide (DMF), to obtain the chloromethylpyridine compound (VI).

The different steps for preparing compound (VI) are preferably continuous ("one pot"), without isolating the intermediate compounds obtained.

Following the method described, it is possible to simply and effectively obtain pantoprazole with good yield.

The invention is illustrated but in no way limited by the following Examples:

EXAMPLES

Example 1

Preparation of Compound (IX)

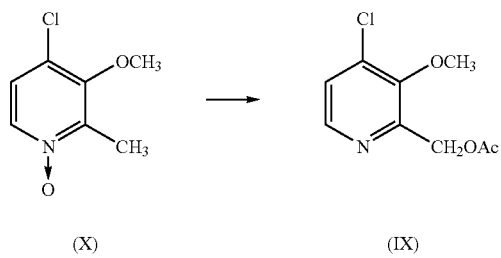

47.5 ml (0.502 mol) of acetic anhydride were mixed with 1.65 g (0.0135 mol) of 4-dimethylaminopyridine, giving a transparent yellow solution which was heated to 65°–70° C. This temperature was held by cooling since the reaction is exothermic. 25 g (0.1441 mol) of 2-methyl-3-methoxy-4-chloropyridine N-oxide (X) were added over a period of about 70 minutes. Once the addition was completed, the reaction was held at 65°–70° C. for a further 2 h 20 minutes and after this time it was allowed to cool down to below 65° C. and 90 ml of methanol were added gradually, while holding the temperature below 65° C. The resulting reaction mass was distilled at reduced pressure in a rotavap to remove the volatile components and the residue containing compound (IX) was used as such for the following reaction. Thin layer chromatography on silica gel 60 F$_{254}$, eluting with CHCl$_3$/MeOH (15:1), showed a single spot at Rf=0.82, indicating that the reaction has been completed.

Example 2

Preparation of Compound (VIII)

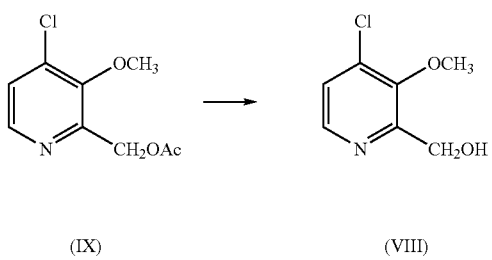

11.5 ml methanol and 11.5 ml of water were added over the crude residue from Example 1 containing compound (IX), and thereafter, while holding the temperature to between 25° and 30° C. with a water bath, the residual acetic acid contained in the crude residue was neutralized by the addition of 33% aqueous NaOH. Once the residual acid had been neutralized, 19 ml (0.2136 mol) of the 33% aqueous NaOH were added over 20 minutes, while holding the temperature to between 25° and 30° C., and, on completion of the addition, the hydrolysis reaction at pH 11.7–11.8 was held for 2 h 30 minutes, to between 25° and 30° C. On completion of the reaction, the pH was adjusted to 7.0–7.5 by the addition of HCl 35%, while holding the temperature to 25° C. Thereafter, 50 ml of methylene chloride were added and, after stirring and allowing to rest, the phases were decanted. A further five extractions were carried out with 30 ml methylene chloride each and the pooled organic phases were dried with anhydrous sodium sulfate, were filtered and washed, and were evaporated at reduced pressure in a rotavap, providing a solid residue having a melting point around 73° C. and containing compound (VIII). Thin layer chromatography on silica gel 60 F$_{254}$, eluting with CHCl$_3$/MeOH (15:1), gave a main spot at Rf=0.55, showing that the reaction was complete. The thus obtained crude residue was used as such in the following reaction.

Example 3

Preparation of Compound (VI)

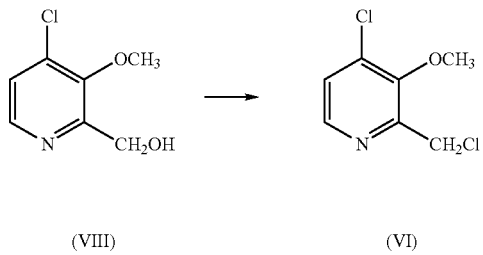

24.5 g of the residue obtained in Example 2, containing approximately 0.142 mol of the compound 2-hydroxymethyl-3-methoxy-4-chloropyridine (VIII), were mixed with 0.5 ml of DMF and 300 ml of anhydrous methylene chloride, to give a brown solution which was cooled to 0°–5° C. in an ice water bath. Thereafter, a solution of 11.5 ml (0.1585 mol) of thionyl chloride in 50 ml of anhydrous methylene chloride was added over 20 minutes, while holding the above-mentioned temperature,. Once the addition was complete, the reaction was held at 0°–5° C. for a further 90 minutes and then 120 ml of water and NaOH 33% were added to pH 5–6, requiring approximately 29 ml of NaOH. The phases were then decanted and separated. The organic phase was extracted with a further 120 ml of water and the pooled aqueous phases were extracted with a further 4×25 ml of methylene chloride, in order to recover the greatest possible amount of product. The pooled organic phases were dried over anhydrous sodium sulfate, filtered and washed, and evaporated at reduced pressure in a rotavap, to give a residue containing the compound 2-chloromethyl-3-methoxy-4-chloropyridine (VI). Thin layer chromatography on silica gel 60 $F_{254}$, eluting with $CHCl_3$/MeOH (15:1), showed a main spot at Rf=0.83, indicating that the reaction was complete. The thus obtained crude residue was used as such in the following reaction.

Example 4

Preparation of Compound (III)

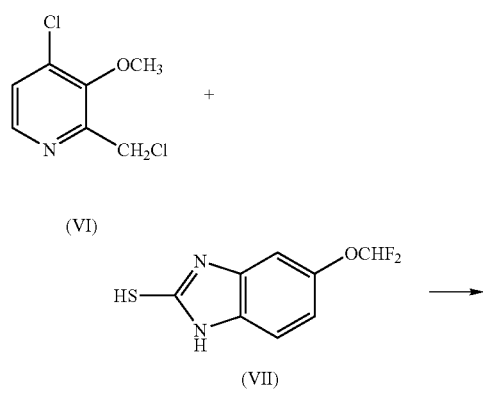

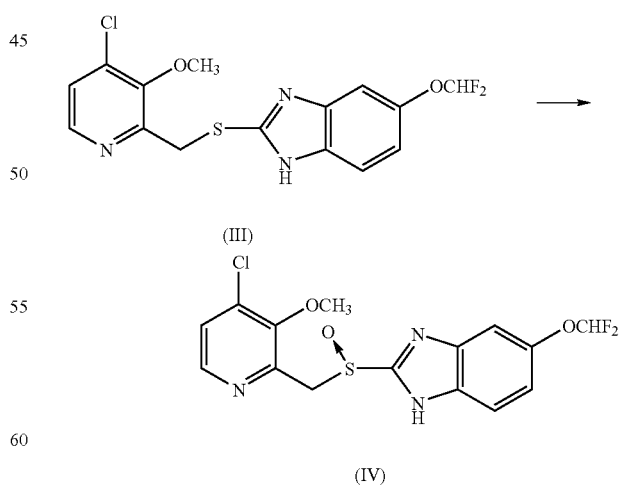

26.11 g of the residue obtained in the Example 3 containing approximately 0.136 mol of the compound 2-chloromethyl-3-methoxy-4-chloropyridine (VI) were mixed with 370 ml of methylene chloride, to give a brown solution over which were added, at 20°–25° C., 29.3 g (0.136 mol) of 5-difluoromethoxy-2-mercaptobenzimidazole (VII) and 17.10 ml (0.136 mol) of tetramethylguanidine (TMGH). The mixture was stirred at this temperature for 2 hours, after which 450 ml of water were added, with the pH being held to between 9.5 and 10. Thereafter the phases were decanted and the organic phase was washed 5×50 ml of a 1N NaOH aqueous solution and, thereafter, with 2×50 ml of water. The organic phase was treated with 50 ml of water and an amount of HCl 30% sufficient to adjust the pH to between 5 and 6. Thereafter, the phases were decanted, and the organic phase was dried over anhydrous sodium sulfate, was filtered and washed, and evaporated at reduced pressure in a rotavap, to give a solid residue of melting point 64°–73° C. that contains the compound (III). Thin layer chromatography on silica gel 60 $F_{254}$, eluting with $CHCl_3$/MeOH (15:1), presented a main spot at Rf=0.52. Yield 82%. The thus obtained compound 5-(difluoromethoxy)-2-[[(3-methoxy-4-chlorine-2 pyridinyl)methyl]mercapto]-1H-benzimidazole (III) was used as such in the following reaction

Example 5

Preparation of Compound (IV)

25.8 g (0.0694 mol) of the compound (III) obtained in the Example 4 were mixed with 88 ml of methanol, to give a brown solution to which 3.7 ml of water, 0.99 g of ammonium molybdate and 0.78 g of sodium carbonate were added. The system was cooled to 0° C.–5° C., 3.4 ml (0.0756 mol) of 60% hydrogen peroxide were added, and the reaction mixture was held at 0° C.–5° C. for 1–2 days, the end point of the reaction being checked by thin layer chromatography on silica gel 60 $F_{254}$, eluting with $CHCl_3$/MeOH (15:1).

During the reaction the presence of hydrogen peroxide in the reaction medium was controlled by testing with potassium iodide, water and starch. When effected on a sample containing hydrogen peroxide, it provides a brown-black colour. If the assay is negative before the chromatographic control indicates completion of the reaction, more hydrogen peroxide is added.

On completion of the reaction, 260 ml of water were added, the system was cooled to 0° C.–5° C. again and the mixture was stirred for 2 hours at this temperature. The solid precipitate was filtered, washed with abundant water, and dried at a temperature below 60° C., to give 5-(difluoromethoxy)-2-[[(3-methoxy-4-chlorine-2-pyridinyl)methyl]sulfinyl]-1H-benzimidazole (IV), melting point 130°–136° C., with an 83.5% yield. Thin layer chromatography on silica gel 60 $F_{254}$, eluting with $CHCl_3$/MeOH (15:1), gave a main spot at Rf=0.5.

Compound (IV) can be purified, if desired, by the following crystallization method:

5 g of crude product was suspended in 16 ml of acetone and was heated to boiling until a dark brown solution was obtained. Thereafter the thus obtained solution was allowed to cool down to room temperature and then was then chilled again to −20° C., at which temperature the mixture was held for 23 hours without stirring. Thereafter the solid was filtered and washed with 6×4 ml of acetone chilled to −20° C. Once dry, the resulting white solid weighed 2.73 g, had a point of melting of 142° C. and gave a single spot in thin layer chromatography. The IR spectrum of the compound on KBr is given in FIG. 1.

The acetonic solution comprising the mother liquors of filtration and the washes was concentrated to a volume of 20 ml and a further 5 g of crude compound were added. The above described crystallization process was repeated to obtain a further 4.11 g of purified product of characteristics similar to the previous one.

The acetonic solution from the previous crystallization was concentrated to a volume of 17 ml and a further 4 g of crude compound were added. The above described crystallization process was repeated to obtain a further 2.91 g of purified product of similar characteristics to the previous ones.

The acetonic solution from the previous crystallization was concentrated to a volume of 15 ml and a further 4 g of crude compound were added. The above described crystallization process was repeated to obtain a further 3.3 g of purified product of similar characteristics to the previous ones.

The acetonic solution from the previous crystallization was concentrated to a volume of 16 ml and a further 4.36 g of crude compound were added. The above described crystallization process was repeated to obtain a further 3.62 g of purified product of similar characteristics to the previous ones.

Finally, the acetonic solution from the previous crystallization was concentrated to a volume of 10–12 ml and held at −20° C. for two-days without stirring. Thereafter, the solid was filtered and washed with 5×3 ml of acetone chilled to −20° C. Once dry, the solid weighed 1.26 g and had similar characteristics to the previous ones.

The total yield of all the crystallizations was 80%.

Example 6

Preparation of Pantoprazole

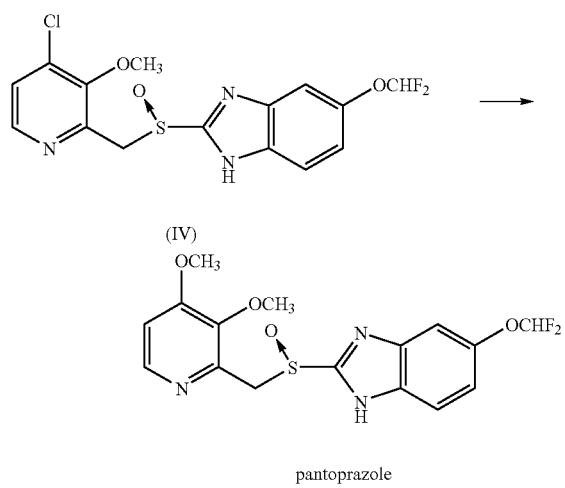

pantoprazole 12.95 g (0.0334 mol) of compound (IV) purified by crystallization of Example 5 were mixed with 38 ml of N,N-dimethylacetamide and thereafter 7.03 g (0.1003 mol) of potassium methoxide were added, while holding the temperature to between 20° C. and 30° C., whereby a dark brown mixture was obtained. The system was held at approximately 25° C. for about 23 hours, after which, once the reaction was complete, the pH was adjusted to 7 with the addition of 3.82 ml of acetic acid. The N,N-dimethylacetamide was removed at reduced pressure at an internal temperature of not more than 75° C. 65 ml of water and 50 ml of methylene chloride were added over the thus obtained residue, followed by decantation of the phases. Once the phases were decanted, the aqueous phase was extracted a with further 3×25 ml of methylene chloride, the organic phases were pooled and the resulting solution dried over anhydrous sodium sulfate, was filtered and washed, and evaporated at reduced pressure in a rotavap, to give a crude residue over which 55 ml of water were added, to give a suspension (if the product does not solidify at this point the water is decanted and a further 55 ml of water are added to remove remains of N,N-dimethylacetamide that hinder the solidification of the product). The solid was filtered and, after drying, 11.61 g of crude pantoprazole of reddish brown colour were obtained (Yield 90%).

The thus obtained crude product was decoloured by dissolving the crude product in 150 ml of methanol, whereby a dark brown solution was obtained. 7.5 g of active carbon were added, while maintaining stirring for 45 minutes at 25° C.–30° C., after which the carbon was filtered out and the filter was washed. The methanol was then removed in the rotavap at reduced pressure, a temperature below 40° C. 10.33 g of a solid residue were obtained and were mixed with 14.9 ml of methylethylketone, and the suspension was heated to 45° C. for about 10 minutes, after which it was cooled, first to room temperature and then to −20° C. This temperature was held over night and thereafter the solid was filtered, washed with 6×5 ml of methylethylketone chilled to −20° C. Once dry, 7.75 g of a white solid, melting point 140° C.–141° C., were obtained. Thin layer chromatography on silica gel F$_{254}$, eluting with CHCl$_3$/MeOH (15:1), gave a single spot at Rf=0.41 and a IR spectrum corresponding identically with that of pantoprazole.

The ketonic solution comprising the mother liquors of filtration and the washes, was concentrated to 9.7 ml, was heated to 40° C., was held at this temperature for about five minutes and was then cooled, first to room temperature and then to −20° C., this temperature being held for 4 hours. At the end of this time, the solid was filtered and was washed with 4×2 ml of methylethylketone chilled to −20° C. Once dry, 0.42 g of a white solid of similar characteristics to the previous one was obtained.

The ketone solution from the previous treatment was concentrated to 3.1 ml, was heated to 40° C., was held to this temperature for about five minutes and then was cooled, first to room temperature and then to −20° C., this temperature being held for 4 hours. At the end of this time, the solid was filtered and was washed with 5×3 ml of methylethylketone chilled to −20° C. Once dry, 0.41 g of a white-beige solid of similar characteristics to the previous one was obtained.

The total yield, including purifications, was 67%.

If a whiter solid is desired, one or several washes can be carried with isopropyl acetate as follows: 6.6 g of pantoprazole from the methylethylketone treatment were suspended in 50 ml of isopropyl acetate. The system (white suspension) was stirred for about 30 minutes at 25° C., was then cooled to 0° C.–5° C., was stirred for about 15 minutes at this temperature and the solid was then filtered, was washed with 3×15 ml of isopropyl acetate. Once dry, 6.26 g of a pure white solid were obtained.

What is claimed is:

1. A process for the preparation of pantoprazole comprising reacting a compound of general formula

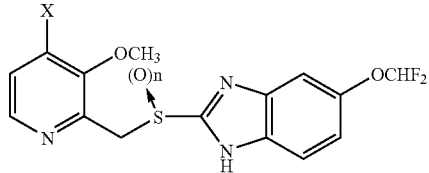

(I)

where x is an atom of halogen and n=1, which
  when n=1 is reacted with a methoxylating agent,
  wherein the methoxylating agent is an alkali metal methoxide,
  wherein the methoxylation is conducted in an aprotic polar solvent, and
  wherein the reaction is carried out at a temperature between room temperature and 800° C.

2. The process for the preparation of pantoprazole according to claim 1, wherein the compound of formula (IV)

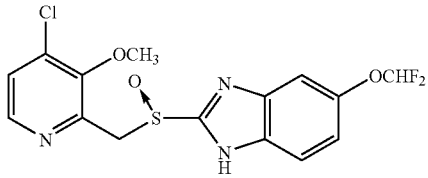

(IV)

is reacted with a methoxylating agent.

3. The process according to claim 1, wherein the methoxylation is conducted in an aprotic polar solvent consisting of N, N-dimethylformamide.

4. The process according to claim 1, wherein the methoxylation is conducted in an aprotic polar solvent consisting of N,N-dimethylacetamide.

* * * * *